United States Patent [19]

Lechtken et al.

[11] Patent Number: 4,710,523

[45] Date of Patent: * Dec. 1, 1987

[54] PHOTOCURABLE COMPOSITIONS WITH ACYLPHOSPHINE OXIDE PHOTOINITIATOR

[75] Inventors: Peter Lechtken, Frankenthal; Ingolf Buethe, Ludwigshafen; Manfred Jacobi, Frankenthal; Werner Trimborn, Limbargerhof, all of Fed. Rep. of Germany

[73] Assignee: BASF Aktiengesellschaft, Ludwigshafen, Fed. Rep. of Germany

[*] Notice: The portion of the term of this patent subsequent to May 5, 1998 has been disclaimed.

[21] Appl. No.: 571,794

[22] Filed: Jan. 18, 1984

Related U.S. Application Data

[63] Continuation of Ser. No. 238,611, Feb. 26, 1981, abandoned, which is a continuation of Ser. No. 148,665, May 12, 1980, Pat. No. 4,298,738, which is a continuation of Ser. No. 55,399, Jul. 6, 1979, abandoned.

[30] Foreign Application Priority Data

Mar. 14, 1979 [DE] Fed. Rep. of Germany ....... 2909994

[51] Int. Cl.$^4$ .......................... C08F 2/50; C08F 4/00; C08L 63/10
[52] U.S. Cl. ........................................ 522/14; 522/16; 522/17; 522/18; 522/26; 522/28; 522/10; 522/50; 522/90; 522/103; 522/107
[58] Field of Search ...................... 204/159.23, 159.24; 522/64, 14, 16, 17, 18, 28, 26

[56] References Cited

U.S. PATENT DOCUMENTS

| | | | |
|---|---|---|---|
| 3,826,640 | 7/1974 | Theissen | 71/86 |
| 4,265,723 | 5/1981 | Hesse et al. | 204/159.23 |
| 4,292,152 | 9/1981 | Lechtken et al. | 430/627 |
| 4,298,738 | 11/1981 | Lechtken et al. | 204/159.23 |
| 4,324,744 | 4/1982 | Lechtken et al. | 204/159.23 |
| 4,385,109 | 5/1983 | Lechtken et al. | 430/281 |

OTHER PUBLICATIONS

Laskorian et al, Chem. Abstracts 82, No. 3, 16,899d, Jan. 20, 1975.

Musierowicz et al, Chem. Abstracts 88, No. 25, 189,901a, Jun. 19, 1978.

Primary Examiner—Melvyn I. Marquis
Assistant Examiner—A. H. Koeckert
Attorney, Agent, or Firm—Keil & Weinkauf

[57] ABSTRACT

Acylphosphine oxide compounds of the general formula

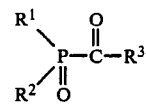

where
R$^1$ is alkyl, cyclohexyl, cyclopentyl, aryl which is unsubstituted or substituted by halogen, alkyl or alkoxy, or an S-containing or N-containing five-membered or six-membered heterocyclic radical,
R$^2$ has one of the meanings of R$^1$ (but R$^1$ and R$^2$ may be identical or different) or is alkoxy, aryloxy or aralkoxy, or R$^1$ and R$^2$ together form a ring and
R$^3$ is an at least disubstituted phenyl, pyridyl, furyl or thienyl radical which carries, at least at the two carbon atoms adjacent to the linkage point of the carbonyl group, the substituents A and B, which may be identical or different, and each of which is alkyl, alkoxy or alkylthio of 1 to 6 carbon atoms, cycloalkyl of 5 to 7 carbon atoms, phenyl or halogen, or R$^3$ is α-naphthyl substituted by A and B at least in the 2- and 8-positions or is β-naphthyl substituted by A and B at least in the 1- and 3-positions, a process for the preparation of these acylphosphine oxide compounds from acid halides of the general formula

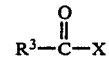

where X is chlorine or bromine, and a phosphine of the general formula

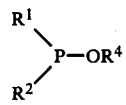

and the use of these acylphosphine oxide compounds as photoinitiators in photopolymerizable surface coatings, finishes and printing inks.

10 Claims, No Drawings

PHOTOCURABLE COMPOSITIONS WITH ACYLPHOSPHINE OXIDE PHOTOINITIATOR

This is a continuation of application Ser. No. 238,611, filed Feb. 26, 1981, now abandoned, which is a continuation of application Ser. No. 148,665, filed May 12, 1980, now U.S. Pat. No. 4,298,738, which is a continuation of application Ser. No. 055,399 filed July 6, 1979, now abandoned.

The present invention relates to novel acylphosphine oxide compounds, their preparation, and their use as photoinitiators in photopolymerizable surface coatings, finishes and printing inks.

A plurality of initiators for the photopolymerization of unsaturated compounds has been disclosed. Hitherto, in the main aromatic ketones, eg. acetophenone and benzophenone derivatives, thioxanthones, benzoin ethers and benzil ketals have been employed. However, compositions hardened with such initiators exhibit an undesirable yellowing, which prevents their use on pale (white) substrates.

A further disadvantage is that the shelf life of the final sensitized resin mixtures is often insufficient and, even when they are stored in the dark, is frequently only a few days.

German Patent Application No. P 28 30 927.5 has proposed acylphosphine oxide compounds as photoinitiators. It is the object of the present invention to provide novel acylphosphine oxide compounds which do not suffer from the above disadvantages of the conventional photoinitiators and also show improvements over the compounds proposed in German Patent Application No. P 28 30 927.5.

We have found that this object is achieved with acylphosphine oxide compounds of the general formula

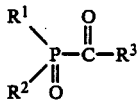

(I)

where $R^1$ is straight-chain or branched alkyl of 1 to 6 carbon atoms, cyclohexyl, cyclopentyl, aryl which is unsubstituted or substituted by halogen, alkyl or alkoxy, or an S-containing or N-containing five-membered or six-membered heterocyclic radical, $R^2$ has one of the meanings of $R^1$ (but $R^1$ and $R^2$ may be identical or different) or is alkoxy of 1 to 6 carbon atoms, aryloxy or aralkoxy, or $R^1$ and $R^2$ together form a ring, and $R^3$ is an at least disubstituted phenyl, pyridyl, furyl or thienyl radical which carries, at least at the two carbon atoms adjacent to the linkage point of the carbonyl group, the substituents A and B, which may be identical or different, and each of which is alkyl, alkoxy or alkylthio of 1 to 6 carbon atoms, cycloalkyl of 5 to 7 carbon atoms, phenyl or halogen, preferably chlorine or bromine, or $R^3$ is α-naphthyl substituted by A and B at least in the 2- and 8-positions or is β-naphthyl substituted by A and B at least in the 1- and 3-positions.

The invention also relates to a process for the preparation of the acylphosphine oxide compounds according to the invention, and to their use as photoinitiators in photopolymerizable surface coatings, finishes and printing inks.

The following details may be noted with respect to the general formula (I) of the acylphosphine oxide compounds according to the invention:

$R^1$ can be straight-chain or branched alkyl of 1 to 6 carbon atoms, eg. methyl, ethyl, i-propyl, n-propyl, n-butyl, amyl and n-hexyl, cyclopentyl, cyclohexyl, aryl, eg. phenyl or naphthyl, halogen-substituted aryl, eg. monochlorophenyl or dichlorophenyl, alkyl-substituted phenyl, eg. methylphenyl, ethylphenyl, isopropylphenyl, tert.-butylphenyl or dimethylphenyl, alkoxy-substituted aryl, eg. methoxyphenyl, ethoxyphenyl or dimethoxyphenyl, or an S-containing or N-containing five-membered or six-membered ring, eg. thienyl or pyridyl.

In addition to having the meanings of $R^1$, $R^2$ can be alkoxy of 1 to 6 carbon atoms, eg. methoxy, ethoxy, i-propoxy, butoxy or ethoxyethoxy, aryloxy, eg. phenoxy or methylphenoxy, or aryl-substituted alkoxy, eg. benzyloxy, and $R^1$ can be joined to $R^2$ to form a ring, as, for example, in acylphosphonic acid o-phenylene esters.

$R^3$ can be 2,6-dimethylphenyl, 2,6-dimethoxyphenyl, 2,6-dichlorophenyl, 2,6-dibromophenyl, 2-chloro-6-methoxyphenyl, 2-chloro-6-methylthiophenyl, 2,4,6-trimethylphenyl, 2,4,6-trimethoxyphenyl, 2,3,4,6-tetramethylphenyl, 2,6-dimethyl-4-tert.-butylphenyl, 1,3-dimethylnaphthalen-2-yl, 2,8-dimethylnaphthalen-1-yl, 1,3-dimethoxynaphthalen-2-yl, 1,3-dichloronaphthalen-2-yl, 2,8-dimethoxynaphthalen-1-yl, 2,4,6-trimethylpyridin-3-yl, 2,4-dimethoxyfuran-3-yl ₁or 2,4,5-trimethylthien-3-yl.

Examples of the photoinitiators according to the invention are methyl 2,6-dimethylbenzoyl-phenylphosphinate, methyl 2,6-dimethoxybenzoyl-phenylphosphinate, 2,6-dimethylbenzoyldiphenylphosphine oxide, 2,6-dimethoxybenzoyl-diphenylphosphine oxide, methyl 2,4,6-trimethylbenzoyl-phenylphosphinate, 2,4,6-trimethylbenzoyl-diphenylphosphine oxide, 2,3,6-trimethylbenzoyl-diphenylphosphine oxide, methyl 2,4,6-trimethylbenzoyl-tolylphosphinate, 2,4,6-trimethoxybenzoyl-diphenylphosphine oxide, ethyl 2,6-dichlorobenzoyl-phenylphosphinate, 2,6-dichlorobenzoyl-diphenylphosphine oxide, 2-chloro-6-methylthiobenzoyl-diphenylphosphine oxide, 2,6-dimethylthiobenzoyl-diphenylphosphine oxide, 2,3,4,6-tetramethylbenzoyl-diphenylphosphine oxide, 2-phenyl-6-methylbenzoyl-diphenylphosphine oxide, 2,6-dibromobenzoyldiphenylphosphine oxide, ethyl 2,4,6-trimethylbenzoylnaphthylphosphinate, ethyl 2,6-dichlorobenzoyl-naphthylphosphinate, 1,3-dimethylnaphthalene-2-carbonyl-diphenylphosphine oxide, 2,8-dimethylnaphthalene-1-carbonyl-diphenylphosphine oxide, 1,3-dimethoxynaphthalene-2-carbonyl-diphenylphosphine oxide, 1,3-dichloronaphthalene-2-carbonyl-diphenylphosphine oxide, 2,4,6-trimethylpyridine-3-carbonyl-diphenylphosphine oxide, 2,4-dimethylfuran-3-carbonyl-diphenylphosphine oxide, 2,4-dimethoxyfuran-3-carbonyl-diphenylphosphine oxide, methyl 2,4,5-trimethylthiophene-3-carbonyl-phenylphosphinate and 2,4,5-trimethyl-thiophene-3-carbonyl-diphenylphosphine oxide.

Particularly preferred compounds are aroyl-phenylphosphinic acid esters and aroyldiphenylphosphine oxides, where the aroyl radical is substituted in the o-positions by alkyl, alkoxy, halogen, alkylthio or a mixture of these, for example 2,6-dimethylbenzoyldiphenylphosphine oxide, 2,4,6-trimethylbenzoyldiphenylphosphine oxide, methyl 2,4,6-trimethylbenzoylphenylphosphinate, 2,6-dichlorobenzoyldiphenylphosphine oxide and 2,6-dimethoxybenzoyldiphenylphosphine oxide.

Compounds of the above type may be prepared by reacting an acid halide of the formula

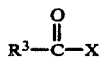

where X is Cl or Br, with a phosphine of the formula

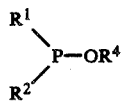

where $R^4$ is straight-chain or branched alkyl of 1 to 6 carbon atoms, or cycloalkyl of 5 or 6 carbon atoms.

The reaction can be carried out in a solvent, for example a hydrocarbon or hydrocarbon mixture, eg. petroleum ether, toluene, cyclohexane, an ether or some other conventional inert organic solvent, or even without a solvent, at from −30° C. to +130° C., preferably at from 10° to 100° C. The product can be directly crystallized out from the solvent, or remains after evaporation, or is distilled under reduced pressure.

The acid halide

and the substituted phosphine $R^1R^2POR^4$ are obtained by processes known to those skilled in the art from the literature (for example Weygand-Hilgetag, Organisch-Chemische Experimentierkunst, 4th edition, pages 246–256, J. A. Barth-Verlag, Leipzig 1970, and K. Sasse in Houben-Weyl, Volume 12/1, pages 208–209, G. Thieme-Verlag, Stuttgart).

The process for the preparation of the compounds according to the invention can for example be represented by the following equation:

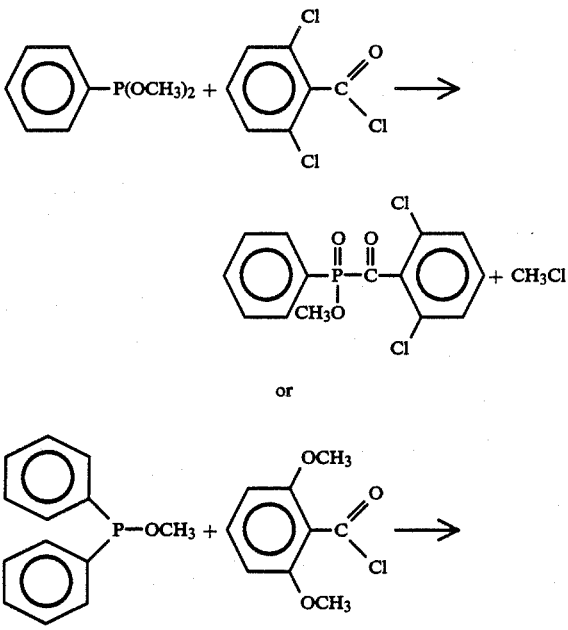

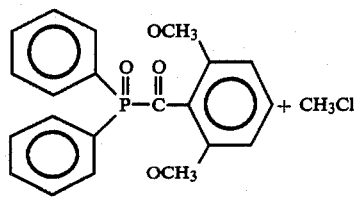

Examples of suitable phosphines are methyldimethoxyphosphine, butyldimethoxyphosphine, phenyldimethoxyphosphine, tolyldimethoxyphosphine, phenyldiethoxyphosphine, tolyldiethoxyphosphine, phenyldiisopropoxyphosphine, tolyldiisopropoxyphosphine, phenyldibutoxyphosphine, tolyldibutoxyphosphine and dimethylmethoxyphosphine, dibutylmethoxyphosphine, dimethylbutoxyphosphine, diphenylmethoxyphosphine, diphenylethoxyphosphine, diphenylpropoxyphosphine, diphenylisopropoxyphosphine, diphenylbutoxyphosphine and similar starting materials which lead to the compounds according to the invention.

Suitable acid halides are the chlorides and bromides, of which the former are particularly preferred.

The compounds having the structure according to the invention exhibit very good reactivity as photoinitiators for photopolymerizable monomers possessing one or more C—C double bonds, and of mixtures of such monomers with one another and with conventional additives. The preferred o-disubstituted aroyldiphenylphosphine oxides and aroyldiphenylphosphinic acid esters, in particular, exhibit excellent shelf life, coupled with very high reactivity, in photopolymerizable monomers. This applies especially to the most commonly used resins based on styrene-containing unsaturated polyesters, and to styrene-free acrylic acid esters. Furthermore, using the initiators according to the invention white-pigmented finishes can be hardened without causing yellowing, but resins with colored pigmentation can equally be employed. In these respects, the novel compounds are superior to the conventional photoinitiators, for example benzil dimethylketal or α-hydroxyisobutyrophenone.

Further, it has been found, surprisingly, that these advantages are retained or even accentuated if the preferred aroyldiphenylphosphine oxides are used in combination with conventional photoinitiators.

Particularly effective synergistic mixtures result on combining the novel compounds with conventional photoinitiators based on aromatic ketones, especially benzil dimethylketal, α-hydroxyisobutyrophenone, diethoxyacetophenone, benzophenone, 2-methylthioxanthone, 2-isopropylthioxanthone and 2-chlorothioxanthone. At the same time, tertiary amines, eg. methyldiethanolamine, may be added to exploit their known accelerating effect. By combining the initiators according to the invention with, for example, benzil dimethylketal it proves possible, surprisingly, to prepare active, amine-free, pigmented or unpigmented photopolymerizable compositions which have very good shelf life.

The photoinitiator of the formula (I) is combined with an aromatic ketone in a ratio of acylphosphine oxide compound:aromatic ketone of from 10:1 to 1:30, preferably from 1:1 to 1:10. The photoinitiator of the formula (I) can be combined with a tertiary amine and with benzophenone and/or thioxanthone either of which may be unsubstituted or substituted by methyl, isopropyl, chlorine or chloromethyl, or with benzil dimethylketal, benzoin isopropyl ether, α-hydroxyisobutyrophenone, diethoxyacetophenone or p-tert.-butyltrichloroacetophenone, with the proviso that the total content of photoinitiator system is from 1% to 20% of the total amount of the photopolymerizable mixture.

Suitable photopolymerizable monomers are the conventional compounds as well as compounds with polymerizable carbon-carbon double bonds which are activated by, for example, aryl, carbonyl, amino, amido, ester, carboxyl or cyanide groups, by halogen atoms or by other carbon-carbon double bonds or carbon-carbon triple bonds. Examples are vinyl ethers and vinyl esters, styrene, vinyltoluene, acrylic acid and methacrylic acid and their esters with monohydric and polyhydric alcohols, their nitriles and their amides, maleic acid esters, fumaric acid esters, N-vinylpyrrolidone, N-vinylcaprolactam, N-vinylcarbazole and allyl esters, eg. diallyl phthalate.

Examples of suitable polymerizable compounds of higher molecular weight are unsaturated polyesters prepared from α,β-unsaturated dicarboxylic acids, eg. maleic acid, fumaric acid or itaconic acid, which may or may not be mixed with saturated or aromatic dicarboxylic acids, eg. adipic acid, phthalic acid, tetrahydrophthalic acid or terephthalic acid, by reacting the acids with alkanediols, eg. ethylene glycol, propylene glycol, butanediol, neopentylglycol or oxyalkylated bisphenol A; epoxide-acrylates, prepared from acrylic acid or methacrylic acid and aromatic or aliphatic diglycidyl ethers, polyester-acrylates (for example prepared from hydroxyl-containing saturated polyesters and acrylic acid or methacrylic acid) and urethane-acrylates.

The photopolymerizable surface coatings, finishes and printing inks can also be in the form of, or be used as, aqueous dispersions.

Saturated and/or unsaturated polymers as well as other adjuvants, eg. thermal polymerization inhibitors, paraffin, pigments, dyes, peroxides, levelling agents, fillers, matting agents and stabilizers against thermal or photochemical degradation, can be added, in the conventional manner, to the photopolymerizable compounds, the formulation of which for any particular end use is familiar to those skilled in the art. Such mixtures are also known to those skilled in the art, and the nature and amount of the adjuvants again depend on the particular end use.

The compounds according to the invention are in general employed at a concentration of from 0.001 to 20%, preferably from 0.1 to 5%, based on the photopolymerizable composition. They may also be combined with accelerators which overcome the inhibiting effect of atmospheric oxygen on the photopolymerization.

Examples of such accelerators or synergistic agents are secondary and/or tertiary amines, eg. methyldiethanolamine, dimethylethanolamine, triethylamine, triethanolamine, ethyl p-dimethylaminobenzoate, benzyldimethylamine, dimethylaminoethyl acrylate, N-phenylglycine, N-methyl-N-phenylglycine and analogous compounds known to those skilled in the art. Aliphatic and aromatic halides, eg. 2-chloromethylnaphthalene and 1-chloro-2-chloromethylnaphthalene, and compounds which form free radicals, eg. peroxides and azo compounds, may also be used to accelerate the hardening process.

Suitable radiation sources for the light which initiated the polymerization of the above mixtures are those which preferably emit in the absorption region of the compounds according to the invention, ie. at from 230 to 450 nm. Particularly suitable sources are low-pressure, medium-pressure and high-pressure mercury lamps, fluorescent tubes and pulsed lamps. The said lamps can, if desired, be doped.

In the Examples which follow, parts and percentages are by weight, unless stated otherwise. Parts by volume bear the same relation to parts as that of the liter to the kilogram.

EXAMPLE 1

225 parts of diphenylchlorophosphine, dissolved in 220 parts by volume of petroleum ether, are added to a mixture of 1,350 parts by volume of petroleum ether (boiling range 40°–70° C.), 180 parts by volume of N,N-diethylaniline and 67 parts by volume of methanol at 0° C., whilst stirring. The mixture is then stirred for a further 2 hours at room temperature. After cooling the mixture to about +5° C., the amine hydrochloride which has separated out is filtered off and the filtrate is first distilled at 10–20 mm Hg, to remove all low-boiling material. The methoxydiphenylphosphine is then fractionally distilled at 0.1–1 mm Hg. Boiling point 120°–124° C./0.5 mm Hg. Yield: 175 parts (80%, based on diphenylchlorophosphine).

648 parts of methoxydiphenylphosphine are added slowly to 547.5 parts of 2,4,6-trimethylbenzoyl chloride at 50°–55° C. in a stirred apparatus equipped with a reflux condenser and dropping funnel. Stirring is continued for 4–5 hours at 50° C., the contents of the flask are dissolved in ether at 30° C., and petroleum ether is added until the mixture begins to turn cloudy. On cooling, 910 parts (87% of theory) of 2,4,6-trimethylbenzoyl-diphenylphosphine oxide crystallize. Melting point: 89°–92° C. The product is in the form of pale yellow crystals.

EXAMPLE 2

20 parts of 2,6-dimethoxybenzoyl chloride are suspended in 20 parts by volume of toluene in the same apparatus as described in Example 1, and 21.6 parts of methoxydiphenylphosphine are added dropwise to this mixture at 50°–55° C., whilst stirring. Stirring is continued for 3 hours at 50° C. and the product is then recrystallized directly from toluene. 32 parts of yellowish crystals are obtained. Melting point: 124°–126° C.

EXAMPLE 3

91 parts of 2,4,6-trimethylbenzoyl chloride are introduced into an apparatus as described in Example 1. 83 parts of triethyl phosphite are added in the course of 15 minutes at 60° C., after which the mixture is stirred for 8 hours at 80° C. The material discharged from the flask is distilled under a pressure of 0.4 mm and the fraction boiling at 120°–122° C. under this pressure is collected. 51 parts (36 percent of theory) of diethyl 2,4,6-trimethylbenzoylphosphonate are obtained as a pale yellowish liquid.

EXAMPLE 4

214 parts of phenyldichlorophosphine are added to a mixture of 1,000 parts by volume of toluene, 421 parts by volume of N,N-diethylaniline and 100 parts by volume of methanol at 0° C. The mixture is then stirred for 1 hour at room temperature, the amine hydrochloride precipitate is filtered off and the filtrate is fractionated. Dimethoxyphenylphosphine distils at 46°–50° C./0.2–0.3 mm.

Yield: 190 parts (93% of theory).

170 parts of dimethoxyphenylphosphine are added dropwise to 182.5 parts of 2,4,6-trimethylbenzoyl chloride at 50° C. The mixture is kept at 50° C. for a further 5 hours, the pale yellowish oil is then dissolved in cyclohexane at 70°–80° C., and the product is caused to crystallize by cooling to 5° C. Pale yellowish crystals are obtained. Melting point 51°–52° C., yield 81% of theory.

Table 1 shows further compounds which were prepared by methods similar to those of Examples 1 to 4.

TABLE 1
Acylphosphine oxide derivatives

|  | Yield | b.p. (mm) | m.p. [°C.] | Analysis C | H | P |
|---|---|---|---|---|---|---|
| 2,4,6-Trimethylbenzoyldiphenyl-phosphine oxide | 87% | — | 80–81 | calc. 75.86 found 75.9 | 6.03 6.1 | 8.91 8.9 |
| Methyl 2,4,6-trimethylbenzoylphenyl-phosphinate | 81% | — | 51–52 | calc. 67.55 found 67.5 | 6.29 6.5 | 10.26 10.1 |
| Diethyl 2,4,6-trimethylbenzoyl-phosphonate | 36% | 120–122 (0.4 mm) | — | calc. 59.15 found 59.3 | 7.39 7.6 | 10.92 10.7 |
| 2,6-Dichlorobenzoyldiphenylphosphine oxide | 82% | — | 154–159 | calc. 60.8 found 60.9 | 3.47 3.7 | 8.27 8.1 |
| 2,4-Dichlorobenzoyldiphenylphosphine oxide | 76% | — | 116–117 | calc. 60.8 found 60.9 | 3.47 3.6 | 8.27 8.3 |
| 2,6-Dimethoxydiphenylphosphine oxide | 88% | — | 124–126 | calc. 68.86 found 68.7 | 5.19 5.4 | 8.47 8.2 |
| 2,3,5,6-Tetramethylbenzoyldiphenyl-phosphine oxide | 63% | — | 123–125 | calc. 76.24 found 76.2 | 6.36 6.5 | 8.56 8.4 |
| 3,4-Dimethylbenzoyldiphenylphosphine oxide | 90% | — | 72–74 | calc. 75.45 found 75.2 | 5.69 5.7 | 9.28 8.9 |

EXAMPLE 5

3 parts of photoinitiator are dissolved in a binder comprising 65 parts of a reaction product of bisphenol A diglycidyl ether and acrylic acid, 35 parts of butane-1,4-diol diacrylate and 3 parts of methyldiethanolamine. The finished mixture is spread as a 60 μm thick layer on a glass plate and is passed at a distance of 10 cm under a high-pressure mercury lamp (output 80 W/cm of arc length) The reactivity is quoted as the maximum possible conveyor belt speed at which the film could be hardened to a scratch-resistant condition.

TABLE 2
Reactivity of the photoinitiators

| Photoinitiator | Reactivity (conveyer speed, m/min.) |
|---|---|
| 2,4-Dichlorobenzoyldiphenylphosphine oxide | <10 |
| 2,6-Dichlorobenzoyldiphenylphosphine oxide | 30 |
| 3,4-Dimethylbenzoyldiphenylphosphine oxide | <10 |
| 2,4,6-Trimethylbenzoyldiphenylphosphine oxide | 70 |
| 2,6-Dimethoxybenzoyldiphenylphosphine oxide | 70 |
| Benzyl dimethylketal | 60 |

2,6-Substituted derivatives thus exhibit a substantially higher reactivity than derivatives where the substituents are present in other positions of the benzoyl radical.

EXAMPLE 6

A surface-coating system similar to that of Example 5 is mixed with a photoinitiator combination shown below and tested as described in Example 5.

| Photoinitiator system | Reactivity (m/min) | Konig pendulum hardness (sec) at 12 m/min |
|---|---|---|
| 3 parts of benzophenone | 12 | 97 |
| 2 parts of benzophenone 1 part of 2,4,6-trimethylbenzoyl-diphenylphosphine oxide | 75 | 213 |
| 3 parts of 2,4,6-trimethylbenzoyl-diphenylphosphine oxide | 70 | 188 |
| 2 parts of benzophenone 1 part of 2,6-dimethoxybenzoyldi-phenylphosphine oxide | 75 | 210 |
| 3 parts of 2,6-dimethoxybenzoyldi-phenylphosphine oxide | 70 | 183 |

EXAMPLE 7

The photoinitiators shown below are dissolved in a mixture of 55 parts of a reaction product of bisphenol A diglycidyl ether and acrylic acid, 45 parts of butanediol diacrylate, 55 parts of rutile pigment and 3 parts of methyldiethanolamine. The finished mixture is spread on a glass plate as an 80 μm thick layer and is passed under two successive Hg high-pressure lamps (each having an output of 80 W/m). The reactivity of the initiator system is characterized by the maximum conveyor belt speed at which the film could be hardened to a scratch-resistant condition.

In a second set of experiments, the above composition is applied as a 200 μm thick layer by means of a knife center. After UV curing, the layer is peeled off the plate and washed with acetone, and the thickness of fully hardened material is then determined. This gives a measure of the depth to which the material

| Photoinitiator | Reactivity (m/min) | Berger whiteness (% reflectance) | Depth to which hardened |
|---|---|---|---|
| 2 parts of 2-methylthio-xanthone | 12 | 66 | 130 μm |
| 1.5 parts of 2-methyl-thioxanthone 0.5 part of 2,4,6-tri-methylbenzoyldiphenyl-phosphine oxide 1.0 part of 2-methylthio-xanthone | 20 | 76 | 140 μm |

-continued

| Photoinitiator | Reactivity (m/min) | Berger whiteness (% reflectance) | Depth to which hardened |
|---|---|---|---|
| 1.0 part of 2,4,6-trimethylbenzoyldiphenylphosphine oxide | 20 | 78 | 140 μm |
| 2 parts of 2,4,6-trimethylbenzoylphosphine oxide | 6 | 81 | 70 μm |

EXAMPLE 8

The photoinitiators to be compared are dissolved in a mixture of 55 parts of a reaction product of bisphenol A diglycidyl ether and acrylic acid, 45 parts of butanediol diacrylate and 55 parts of rutile pigment. The surface-coating mixture is spread as an 80 μm thick layer on a glass plate and is hardened as described in Example 7. It is found that benzil dimethylketal or α-hydroxyisobutyrophenone alone do not harden the pigmented surface-coating. However, they can replace part of the initiator according to the invention, ie. 2,4,6-trimethylbenzoyldiphenylphosphine oxide, without substantial decrease in the degree of hardening.

| Initiator | Concentration | Pendulum hardness in sec. at a conveyor belt speed of 6 m/min | 12 m/min |
|---|---|---|---|
| 2,4,6-Trimethylbenzoyldiphenylphosphine oxide | 3% | 81 | 56 |
| 2,4,6-Trimethylbenzoyldiphenylphosphine oxide | 2% | 78 | 43 |
| α-Hydroxyisobutyrophenone | 1% | | |
| 2,4,6-Trimethylbenzoyldiphenylphosphine oxide | 2% | 71 | 61 |
| Benzil dimethylketal | 1% | | |
| α-Hydroxyisobutyrophenone | 3% | In each case only dry at the surface | |
| Benzil dimethylketal | 3% | | |

EXAMPLE 9

An unsaturated polyester is prepared by esterifying 431 parts of maleic anhydride and 325 parts of phthalic anhydride with 525 parts of 1,2-propylene glycol. After adding 0.01% of hydroquinone, a 66% strength solution of the polyester in styrene is prepared, and the particular photoinitiator is dissolved in this solution.

To carry out the light-hardening experiments, 10 parts of a 1% strength solution of paraffin (softening range 50°–52° C.) in styrene are added to 100 parts of the above mixture and the resin is applied to a glass plate by means of a film spreader with a clearance of 400 μm. After air-drying for about one minute, the film is exposed to fluorescent lamps (Philips TLA05/40 W) mounted at a distance of 4 cm. The test is repeated after having stored the photopolymerizable mixture in the dark for 5 days at 60° C. The following results are obtained, in each case after an exposure time of 2 minutes.

| Photoinitiator | Concentration | Konig pendulum hardness (sec) immediate | after 5 days at 50° C. |
|---|---|---|---|
| 2,4,6-Trimethylbenzoyldiphenylphosphine oxide | 1% | 73 | 73 |
| 2,6-Dimethoxybenzoyldiphenylphosphine oxide | 2% | 62 | 60 |
| Pivaloyldiphenylphosphine oxide (for comparison) | 2% | 60 | 10 |
| Benzil dimethylketal (for comparison) | 2% | 45 | 40 |
| α-Hydroxyisobutyrophenone (for comparison) | 2% | 20 | 19 |

EXAMPLE 10

An unsaturated polyester resin is prepared by esterifying 143 parts of tetrahydrophthalic anhydride and 175 parts of maleic anhydride with 260 parts of diethylene glycol; a 64% strength solution of the resin in styrene is made up and stabilized with 0.01% of hydroquinone.

To carry out the light-hardening experiments, 20 parts of TiO$_2$, 10 parts of a 1% strength paraffin solution in styrene and the particular initiator, in the stated amount, are added to 100 parts of the above solution. A 60 μm thick layer of the resin is applied to a glass plate by means of a knife coater and is immediately irradiated for 20 seconds under a high-pressure Hg lamp (100 W/cm arc length) at a distance of 10 cm. The following results are obtained:

| Photoinitiator | Concentration of initiator | Konig pendulum hardness (sec) |
|---|---|---|
| 2,4,6-Trimethylbenzoyldiphenylphosphine oxide | 1% | 126 |
| 2,6-Dimethoxybenzoyldiphenylphosphine oxide | 1% | 81 |
| 3,4-Dimethylbenzoyldiphenylphosphine oxide | 2% | 20 |
| Benzil + methyldiethanolamine | 2% + 4% | 32 |

Whilst the resins sensitized with the initiators according to the invention show no significant decrease in reactivity after storage for 5 days at 60° C., the batch containing benzil/amine has already gelled after that time.

EXAMPLE 11

15 parts of an 0.7% strength solution of paraffin (melting point 50°–52° C.) in styrene, in which the photoinitiator has also been dissolved, are added to 100 parts of a resin prepared as described in Example 10. 3% of a colored pigment are then added to the resin, 100 μm thick films are applied to glass plates by means of a knife coater, and the films are exposed for 20 seconds by the method described in Example 10. The results show that the initiators according to the invention can also be used to harden surface-coatings containing colored pigments, and to harden printing inks, even when combined with conventional initiators which are of little or no use for the same purpose, ie. they show a synergistic effect.

| Initiator | Konig pendulum hardness in sec., mixture pigmented with | | |
|---|---|---|---|
| | Heliogen-grun 8721 | Heliogen-blau 7080 | Lithol-scharlach 4300 |
| 2 parts of 2,4,6-trimethyl-benzoyldiphenylphosphine oxide | 123 | 129 | 161 |
| 1 part of 2,4,6-trimethyl benzoyldiphenylphosphine oxide / 1 part of benzil dimethyl-ketal | 129 | 125 | 170 |
| 2 parts of benzil dimethyl-ketal | 49 | Only surface-hardened | 169 |

We claim:

1. A process for the preparation of photopolymerizable surface-coatings, finishes and printing inks wherein an acylphosphine oxide compound of the general formula

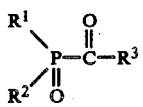

where $R^1$ is straight-chain or branched alkyl of 1 to 6 carbon atoms, cyclohexyl, cyclopentyl, phenyl or naphthyl which is unsubstituted or substituted by halogen, alkyl of 1 to 6 carbon atoms, or an S-containing or N-containing five-membered or six-membered heterocyclic radical selected from pyridyl or thienyl, $R^2$ has one of the meanings of $R^1$ with the proviso that $R^1$ and $R^2$ may be identical or different, or $R^2$ is alkoxy of 1 to 6 carbon atoms, phenoxy, methylphenoxy or benzyloxy, or $R^1$ and $R^2$ may be joined together to form a five- or six-membered P-containing ring, and $R^3$ is an at least disubstituted phenyl, pyridyl, furyl or thienyl radical which carries, at least at the two carbon atoms adjacent to the linkage point of the carbonyl group, the substituents A and B, which may be identical or different, and each of which is alkyl, alkoxy or alkylthio of 1 to 6 carbon atoms, cycloalkyl of 5 to 7 carbon atoms, phenyl or halogen, or $R^3$ is α-naphthyl subsituted by A and B at least in the 2- and 8-positions or is α-naphthyl substituted by A and B at least in the 1 and 3 positions, is mixed as a photoinitiator in a concentration of from 0.001% to 20% by weight of the total amount of the photopolymerizable mixture with at least one photopolymerizable material containing at least one carbon-carbon polymerizable double bond and at least one aryl, carbonyl, amino, amido, ester, carboxyl or cyanide group or halogen atom or additional carbon-carbon double bond or carbon to carbon triple bond in photopolymerization activating relationship to the said carbon-carbon polymerizable double bond.

2. The process of claim 1 wherein $R^3$ in the formula (I) is 2,4,6-trimethylphenyl and $R^1$ and $R^2$ are each phenyl.

3. The process of claim 1 wherein $R^1$ and $R^2$ in the formula (I) are phenyl or $C_1$–$C_6$-alkyl-substituted phenyl.

4. The process of claim 1 wherein the photoinitiator is combined with secondary or tertiary amines.

5. The process of claim 2 wherein the photoinitiator is combined with secondary or tertiary amines.

6. The process of claim 3 wherein the photoinitiator is combined with secondary or tertiary amines.

7. The process of claim 1 wherein the photoinitiator of the formula (I) is combined with an aromatic ketone in a ratio of acylphosphine oxide compound:aromatic ketone of from 1:1 to 1:10.

8. The process of claim 7 wherein a tertiary amine in a concentration of from 0.5 to 15% is added as the accelerator.

9. The process of claim 1 wherein the acylphosphine oxide compound is combined with a tertiary amine and with benzophenone or thioxanthone or with both benzophenone and thioxanthone, either of which may be unsubstituted or substituted by methyl, isopropyl, chlorine or chloromethyl, or with benzil dimethylketal, benzoin isopropyl ether, α-hydroxyisobutyrophenone, diethoxyacetophenone or p-tert.-butyltrichloroacetophenone, with the proviso that the total content of photoinitiator system is from 1% to 20% of the total amount of the photopolymerizable mixture.

10. The process of claim 1, wherein the photopolymerizable material is selected from the group consisting of unsaturated polyester, epoxy acrylate, polyesteracrylate and urethane acrylate.

* * * * *